United States Patent
Colby et al.

(10) Patent No.: US 9,604,902 B2
(45) Date of Patent: Mar. 28, 2017

(54) SELECTIVE SYNTHESIS OF 2-OCTYL ACRYLATE BY ACID CATALYZED ESTERIFICATION OF 2-OCTANOL AND ACRYLIC ACID

(71) Applicant: 3M INNOVATIVE PROPERTIES COMPANY, St. Paul, MN (US)

(72) Inventors: Joshua L. Colby, Lino Lakes, MN (US); Tabitha A. Clem, Woodbury, MN (US); Terence D. Spawn, Stillwater, MN (US); Aaron E. Hutt, St. Paul, MN (US); Wade T. Teply, Crystal, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/769,875

(22) PCT Filed: Mar. 4, 2014

(86) PCT No.: PCT/US2014/020213
§ 371 (c)(1),
(2) Date: Aug. 24, 2015

(87) PCT Pub. No.: WO2014/149669
PCT Pub. Date: Sep. 25, 2014

(65) Prior Publication Data
US 2016/0002140 A1 Jan. 7, 2016

Related U.S. Application Data

(60) Provisional application No. 61/789,297, filed on Mar. 15, 2013.

(51) Int. Cl.
*C07C 67/08* (2006.01)
*C09J 133/08* (2006.01)
*C08F 220/18* (2006.01)
*C07C 57/02* (2006.01)

(52) U.S. Cl.
CPC .............. *C07C 67/08* (2013.01); *C07C 57/02* (2013.01); *C08F 220/18* (2013.01); *C09J 133/08* (2013.01); *Y02P 20/582* (2015.11)

(58) Field of Classification Search
CPC .................................. C07C 67/08; C07C 69/54
See application file for complete search history.

(56) References Cited

U.S. PATENT DOCUMENTS

| | | | |
|---|---|---|---|
| 4,619,979 A | 10/1986 | Kotnour | |
| 4,737,559 A | 4/1988 | Kellen | |
| 4,833,267 A | 5/1989 | Nakashima et al. | |
| 4,843,134 A | 6/1989 | Kotnour | |
| 5,637,646 A | 6/1997 | Ellis | |
| 5,804,610 A | 9/1998 | Hamer | |
| 5,892,103 A * | 4/1999 | Sogabe | B01J 8/005 560/205 |
| 6,893,718 B2 | 5/2005 | Melancon | |
| 7,385,020 B2 | 6/2008 | Anderson et al. | |
| 7,893,179 B2 | 2/2011 | Anderson et al. | |
| 8,318,303 B2 | 11/2012 | Lu | |
| 2009/0156074 A1 | 6/2009 | Lu | |
| 2010/0151241 A1* | 6/2010 | Hardy | C09J 133/08 428/355 AC |
| 2012/0329898 A1 | 12/2012 | Weikel | |
| 2013/0023622 A1 | 1/2013 | Lu | |

FOREIGN PATENT DOCUMENTS

| | | |
|---|---|---|
| CN | 87105726 | 7/1988 |
| CN | 101517026 | 8/2009 |
| WO | WO 2009-129087 | 10/2009 |
| WO | WO 2012-088126 | 6/2012 |
| WO | WO 2013/004767 | 1/2013 |

OTHER PUBLICATIONS

Kabza et al. (J. Org. Chem. 2000, 65, 1210-1214).*
ASTM D6866-12, "Standard Test Methods for Determining the Biobased Content of Solid, Liquid, and Gaseous Samples Using Radiocarbon Analysis", 14 pages, Jan. 2013.
International Search Report for PCT International Application No. PCT/US2014/020213, mailed on Aug. 28, 2014.

* cited by examiner

*Primary Examiner* — Vu A Nguyen
(74) *Attorney, Agent, or Firm* — Adrian L. Pishko

(57) ABSTRACT

A method of making 2-octyl acrylate comprising reacting 2-octanol with acrylic acid in the presence of an acid catalyst and added water is described. The 2-octanol may be derived from renewable resources, such as castor oil. The method is efficient and provides selectivity for 2-octyl acrylate.

15 Claims, No Drawings

SELECTIVE SYNTHESIS OF 2-OCTYL ACRYLATE BY ACID CATALYZED ESTERIFICATION OF 2-OCTANOL AND ACRYLIC ACID

CROSS REFERENCE TO RELATED APPLICATIONS

This application is a national stage filing under 35 U.S.C. 371 of PCT/US2014/020213, filed Mar. 4, 2014, which claims priority to U.S. Application No. 61/789,297, filed Mar. 15, 2013, the disclosure of which is incorporated by reference in its/their entirety herein.

TECHNICAL FIELD

The present disclosure relates to selectively synthesizing 2-octyl acrylate including acid catalyzed esterification of 2-octanol and acrylic acid.

BACKGROUND

Pressure sensitive adhesives (PSAs) are known to possess properties including the following: (1) aggressive and permanent tack, (2) adherence with no more than finger pressure, (3) sufficient ability to hold onto an adherend or substrate, and (4) sufficient cohesive strength to be removed cleanly from the adherend. Materials that have been found to function well as PSAs include polymers designed and formulated to exhibit the requisite viscoelastic properties resulting in a desired balance of tack, peel adhesion, and shear holding power. PSAs are characterized by being normally tacky at room temperature (e.g., 20° C.). PSAs do not embrace compositions merely because they are sticky or adhere to a surface.

Only a limited number of classes of polymers have been found to function as PSAs. Among these polymer classes are natural and synthetic rubbers, (meth)acrylic polymers, silicones, block copolymers and olefins. Acrylic polymers have proven especially useful. Acrylic based PSAs are frequently prepared from isooctyl acrylate or 2-ethylhexyl acrylate. These adhesives have many desirable attributes such as high peel adhesion when applied to a wide variety of surfaces.

Further, acrylic PSAs are generally derived from petroleum feedstocks. The increase in the price of oil, and concomitant petroleum-derived products, has led to volatile prices and supply for many adhesive products. It is desirable to replace all or part of the petroleum-based feedstocks with those derived from renewable sources, such as plants, as such materials become relatively cheaper, and are therefore both economically and socially beneficial. Therefore, the need for such plant-derived materials has become increasingly significant.

Current methods for preparing 2-octyl acrylate from plant-derived materials include batch esterification of acrylic acid and 2-octanol at elevated temperature and reduced pressure, employing long reaction times. There exists a need for a process to selectively and efficiently prepare 2-octyl acrylate from plant-derived materials.

SUMMARY

Briefly, in one aspect, the present disclosure describes a method of making 2-octyl acrylate comprising reacting 2-octanol with acrylic acid in the presence of an acid catalyst and added water.

In another aspect, the present disclosure describes 2-octyl acrylate made by a method comprising reacting 2-octanol with acrylic acid in the presence of an acid catalyst and added water.

In a further aspect, the present disclosure describes a method of making an adhesive comprising (a) reacting 2-octanol with acrylic acid in the presence of an acid catalyst and added water, thereby forming 2-octyl acrylate and (b) reacting at least some of the 2-octyl acrylate with at least one initiator and at least one (meth)acrylic acid comonomer, thereby forming the adhesive.

Various unexpected results and advantages are obtained in exemplary embodiments of the disclosure. One such advantage of exemplary embodiments of the present disclosure is that 2-octyl acrylate is produced quickly using a selective method of esterifying biobased 2-octanol and (optionally biobased) acrylic acid, for example by using a continuous method employing an acid catalyst. The selectivity of the esterification reaction contributes to the rate of production of the 2-octyl acrylate by minimizing steps, such as multiple purification and recycling steps to separate 2-octyl acrylate from production byproducts (e.g., octene isomers, 3-octyl acrylate, and 4-octyl acrylate). Further, in embodiments in which the acid catalyst comprises a heterogeneous catalyst, the process does not require catalyst neutralization and/or filtration steps.

Various aspects and advantages of exemplary embodiments of the disclosure have been summarized. The above Summary is not intended to describe each embodiment or every implementation of the present certain exemplary embodiments of the present disclosure. The Detailed Description that follows more particularly exemplifies certain preferred embodiments using the principles disclosed herein.

DETAILED DESCRIPTION

For the following Glossary of defined terms, these definitions shall be applied for the entire application, unless a different definition is provided in the claims or elsewhere in the specification.

GLOSSARY

Certain terms are used throughout the description and the claims that, while for the most part are well known, may require some explanation. It should understood that, as used herein:

As used in this specification and the appended embodiments, the singular forms "a", "an", and "the" include plural referents unless the content clearly dictates otherwise. Thus, for example, reference to fine fibers containing "a compound" includes a mixture of two or more compounds. As used in this specification and the appended embodiments, the term "or" is generally employed in its sense including "and/or" unless the content clearly dictates otherwise.

As used in this specification, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

The term "(co)polymer" is inclusive of both homopolymers containing a single monomer and copolymers containing two or more different monomers.

The term "(meth)acrylic" or "(meth)acrylate" is inclusive of both acrylic and methacrylic (or acrylate and methacrylate).

The term "aliphatic group" means a saturated or unsaturated linear or branched hydrocarbon group. This term is used to encompass alkyl, alkenyl, and alkynyl groups, for example.

The term "alkyl group" means a saturated linear or branched hydrocarbon group including, for example, methyl, ethyl, isopropyl, t-butyl, heptyl, octyl, dodecyl, octadecyl, amyl, 2-ethylhexyl, and the like. The term "alkylene group" refers to a divalent alkyl group.

The term "heteroalkyl group" means an alkyl group having at least one —$CH_2$— replaced with a heteroatom such as O or S. In many embodiments, the heteroalkyl group is a monovalent polyether group. The term "heteroalkylene group" refers to a divalent heteroalkyl group. In many embodiments, the heteroalkylene group is a divalent polyether group.

The term "alicyclic group" means a cyclic hydrocarbon group having properties resembling those of aliphatic groups. The term "aromatic group" or "aryl group" means a mono- or polynuclear aromatic hydrocarbon group.

When a group is present more than once in a formula described herein, each group is "independently" selected, whether specifically stated or not. For example, when more than one R group is present in a formula, each R group is independently selected.

The term "continuous" process refers to a process with non-interrupted flow or semi-non-interrupted flow (i.e., pulsed flow) of material(s) in and out of the reactor once the system is operating at steady state. Preferably, a "continuous reactor" refers to a fixed-bed reactor comprising a heterogeneous catalyst with a non-interrupted flow of reactants. In a continuous process of this disclosure, a reactor, typically a tubular reactor, having an inlet for reactants and an outlet for products is charged with a fixed bed of solid acid catalyst and used to perform the desired chemical transformation(s). This reactor configuration, often described as a "packed-bed reactor," can be advantageous when compared to homogeneously catalyzed batch reactions for a number of reasons including: ease of reaction; tighter control over process variables (e.g., temperature, pressure and residence time); higher catalyst to reagent ratio (facilitating higher rates of reaction); and elimination of a catalyst filtration and/or neutralization step. As an alternative to using a packed-bed reactor configuration, other well known continuous reactor configurations may be employed such as "continuous stirred tank" reactors or "reactive distillation" reactors.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment," "in many embodiments" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

A wide variety of commercially available solid (typically, resin) acid catalysts may be used with a packed-bed reactor, for example, in a continuous process. In particular, solid acid (heterogeneous) catalysts may be advantageously used in performing the desired chemical transformation(s) disclosed herein including, but not limited to, sulfonated styrene divinylbenzene copolymers (e.g., those available under the trade name AMBERLYST, for instance AMBERLYST 70 or AMBERLYST 46) and high fluorine content aliphatic sulfonic acids (e.g., those available under the trade name NAFION). Selection of a suitable solid acid catalyst material is typically determined by cost, rate of reaction, and selectivity to desired products. One particular type of resin, macroreticular resin, is particularly preferred because it is inexpensive and available in a wide variety of different physical and/or chemical structures. Varying catalyst features such as catalyst surface area, porosity, and acidity can be tuned by varying resin properties such as the extent of crosslinking and degree of sulfonization, facilitating the selection of a suitable catalyst for each desired reaction. Selection of such features is within the skill of one skilled in the art.

AMBERLYST 70 is one suitable cation exchange resin, and has a halogenated interface between the sulfonic acid catalyst group and the polymer resin that provides temperature stability, and may also affect reactivity. AMBERLYST 46 is another suitable cation exchange resin, which only contains acidic groups at the exterior of the spherical resin particles, thereby increasing the selectivity of certain reactions by minimizing exposure of products to catalyst sites while exiting the porous resin. The rate of reaction using AMBERLYST 46 will likely be slower than using AMBERLYST 70, due at least to the fewer number of acidic groups. A further suitable cation exchange resin is AMBERLYST 15, which is also a strongly acidic ion exchange resin. Moreover, PUROLITE CT275 (available from Purolite International Limited, Pontyclun, Wales) is a suitable catalyst that is also a strongly acidic ion exchange resin, and has a relatively large pore diameter (e.g., a median pore diameter of 0.425-1.200 millimeters).

Various exemplary embodiments of the disclosure will now be described. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

Thus, in one exemplary embodiment, the disclosure provides a method of making 2-octyl acrylate comprising reacting 2-octanol with acrylic acid in the presence of an acid catalyst and added water. For example and without limitation, embodiments of the method comprise charging a reactor tube with an acid catalyst material, followed by a pre-mixture of 2-octanol and acrylic acid containing added water being fed to the reactor continuously at a predetermined temperature and pressure. For example, a liquid syringe pump would be suitable for delivering the mixture of reactants to the reactor tube. After allowing several residence times of the reactants in the reactor to reach steady state, product is collected for analysis of, for instance, a mixture of primarily octanol, acrylic acid, octene isomers, and octyl acrylate isomers, and water.

In one exemplary continuous process, 2-octanol and acrylic acid reactants (as described herein) are mixed prior to entering or upon entering the reaction zone, defined to be the volume in the tubular reactor occupied by the heterogeneous catalyst material. Time required to perform the desired reaction can vary, primarily due to catalyst type and temperature. Reactant residence time, defined as the catalyst void volume divided by the volumetric feed rate of the reactants, may be controlled, for example, by adjusting the total reactant feed rate to the reactor. Reactant residence time is typically held constant at values of at least 1 minute, and often at least 5 minutes. Reactant residence time is typically held constant at values of no greater than 120 minutes, and often no greater than 20 minutes. Reaction temperatures may be controlled with resistively heated insulating tape or by circulating heating oil from a temperature controlled bath, or other conventional methods.

In many embodiments, the esterification of 2-octanol and acrylic acid to produce of 2-octyl acrylate is performed in a continuous reactor at a weight hourly space velocity (WHSV) of 0.1 hour$^{-1}$ (h$^{-1}$) ($2.8 \times 10^{-5}$ seconds$^{-1}$) to 3 h$^{-1}$ ($8.3 \times 10^{-4}$ s$^{-1}$), or 0.3 h$^{-1}$ ($8.3 \times 10^{-4}$ s$^{-1}$) to 1 h$^{-1}$ ($2.8 \times 10^{-4}$ s$^{-1}$), or 0.5 h$^{-1}$ ($1.4 \times 10^{-4}$ s$^{-1}$) to 1.5 h$^{-1}$ ($4.2 \times 10^{-4}$ s$^{-1}$), or 0.5 h$^{-1}$ ($1.4 \times 10^{-4}$ s$^{-1}$) to 2 h$^{-1}$ ($5.6 \times 10^{-4}$ s$^{-1}$), or 0.2 h$^{-1}$ ($5.6 \times 10^{-5}$ s$^{-1}$) to 0.7 h$^{-1}$ ($1.9 \times 10^{-4}$ s$^{-1}$). The WHSV, as used herein, is defined as a ratio of the mass flow of 2-octanol and acrylic acid entering the system per hour, to the mass of the acid catalyst in the continuous reactor. It is to be understood that the phrase "the mass of the acid catalyst" as used throughout this disclosure refers to the mass of the entire catalyst material (including both the support structure and the acid functional groups for a heterogeneous acid catalyst, for example). In other words, the WHSV is a ratio of mass flow of 2-octanol and acrylic acid entering the system per hour to the mass of the catalyst material.

In certain embodiments the acid catalyst comprises a heterogeneous acid catalyst, for example and without limitation a cation exchange resin. As noted above, suitable cation exchange resins include those commercially available from Dow Chemical Company (Midland, Mich.) under the trade name AMBERLYST. In certain embodiments, AMBERLYST 70 is a particularly preferred heterogeneous acid catalyst. In some embodiments the acid catalyst comprises a material such as a polymer, zeolite, metal oxides (e.g., zirconia), or other solid structural material having acidic functional groups affixed thereto. Suitable acid catalysts comprise acidic functional groups, such as comprising sulfonic acid.

In select embodiments, the acid catalyst comprises a liquid homogeneous acid catalyst. Suitable liquid homogeneous acid catalysts include for example and without limitation trifluoromethanesulfonic acid, nonafluorobutanesulfonic acid, p-toluenesulfonic acid, sulfuric acid, and/or methanesulfonic acid.

The relative amounts of reactants 2-octanol and acrylic acid are provided, in certain aspects, in a 10:1 to a 1:10 molar ratio, for instance the 2-octanol and acrylic acid may be provided in a 3:1 to a 1:3 molar ratio, or a 2:1 to a 1:2 molar ratio, or a 1:1 molar ratio.

At high acid catalyst activity and high temperatures, it was discovered that 2-octanol could be more selectively dehydrated to octene than esterified to 2-octyl acrylate. Unexpectedly, the inclusion of added water with the reactant feed improves selectivity of the reaction to form 2-octyl acrylate, as compared to the same reaction absent added water. Moreover, the rate of octyl acrylate formation is substantially maintained when water is added to the reactant feed. Without wishing to be bound by theory, it is believed that the water decreases the effective acidity of the acid functional groups of the acid catalyst by hydrating the acid functional groups, thereby decreasing the activity of the acid catalyst. In most embodiments, added water comprises 0.1 to 10 percent by weight of the total reactants, or 0.1 to 5 percent by weight, or 1 to 5 percent by weight, or 1 to 3 percent by weight, or 2 to 4 percent by weight of the total reactants.

In certain embodiments, the yield of the reaction to form 2-octyl acrylate is such that 15 to 70% by weight of the 2-octanol is converted to 2-octyl acrylate, or 20 to 40% by weight, or 50 to 70% by weight, or 30 to 70% by weight of the 2-octanol is converted to 2-octyl acrylate.

The reaction is performed at a suitable temperature, for example a temperature of 60° C. to 130° C., or 60° C. to 100° C., or 100° C. to 130° C., or 80° C. to 110° C. Upon increasing the temperature, the reaction rate tends to increase significantly, however, at higher temperatures there may be more competing reactions on the acid catalyst functional sites.

The reaction to form 2-octyl acrylate is performed at any suitable reaction pressure, for instance at a pressure in the range of atmospheric pressure 14.7 psig (0.20 MPa) to 100 pounds per square inch gauge (psig) (0.79 MPa). In certain embodiments, the reaction is performed at a pressure of 10 psig (0.17 MPa) to 50 psig (0.44 MPa), or 55 psig (0.48 MPa) to 100 psig (0.79 MPa), or 10 psig (0.17 MPa) to 30 psig (0.31 MPa). These pressures will typically keep reagents in the liquid phase while reducing the need for specialized equipment that can withstand elevated pressures.

In many embodiments, 2-octyl acrylate is made by a method comprising reacting 2-octanol with acrylic acid in the presence of an acid catalyst and added water. The materials and conditions of the method are as described herein. For instance, the acid catalyst comprises either a heterogeneous sulfonic acid catalyst (e.g., a cation exchange resin) or a homogeneous sulfonic acid catalyst. The 2-octanol and acrylic acid are provided in a 10:1 to 1:10 molar ratio, such as in a 1:3 to 3:1 molar ratio, or 1:1 molar ratio. The 2-octanol is preferably derived from at least one plant oil, for instance from castor oil.

As noted above, each of the 2-octanol and the acrylic acid reactants is preferably biobased. ASTM D6866-12, "Determining the Biobased Content of Solid, Liquid, and Gaseous Samples Using Radiocarbon Analysis," provides methods for determining the source of carbon in a material using carbon dating. In particular, $^{14}$C/C and $^{13}$C/C isotopic ratios indicate if a material has a fossil (e.g., petroleum based) carbon source or a plant based carbon source. A material with a fossil carbon source contains no $^{14}$C, whereas a material with 100% $^{14}$C (after correction for 1950s nuclear testing) indicates a completely modern, biobased carbon source. In most embodiments, the 2-octyl acrylate comprises between 50% and 100% by weight biobased carbon, as determined using ASTM D6866-12, or between 70% and 100% by weight biobased carbon. Amounts towards the upper ends of these ranges are achievable when a biobased acrylic acid is used in the esterification reaction. Concomitantly, in embodiments in which the 2-octanol is biobased but the acrylic acid is not, the resulting 2-octyl acrylate comprises an amount of biobased carbon towards the lower ends of these ranges.

Alternatively, the biobased content of the 2-octanol employed in the esterification reaction is expressed as a $^{14}C/C$ ratio. In certain embodiments, the 2-octanol comprises a $^{14}C/C$ ratio of $1.0 \times 10^{-14}$ or higher, or of $1.0 \times 10^{-13}$ or higher, or of $1.0 \times 10^{-12}$ or higher.

In certain embodiments, biobased 2-octanol is derived from at least one plant oil, for example from castor oil. The 2-octanol may be prepared by treatment of ricinoleic acid, derived from castor oil, (or an ester or acyl halide thereof) with sodium hydroxide, followed by distillation from the co-product sebacic acid. A suitable biobased 2-octanol is commercially available from Alnor Oil Company, Inc. (Valley Stream, N.Y.).

The method of certain embodiments producing 2-octyl acrylate further comprises separating unreacted 2-octanol feed from the 2-octyl acrylate using distillation. Unreacted 2-octanol is preferably recycled back to the reactant feed. Typically, the 2-octyl acrylate produced is further processed, for example by purifying the 2-octyl acrylate. Whether or not the 2-octyl acrylate produced is purified, it is preferably reacted with at least one initiator and at least one (meth) acrylic acid comonomer, thereby forming an adhesive. Accordingly, in some embodiments a method of making an adhesive is provided comprising reacting 2-octanol with acrylic acid in the presence of an acid catalyst and added water, thereby forming 2-octyl acrylate, and reacting at least some of the 2-octyl acrylate with at least one initiator and at least one (meth)acrylic acid comonomer, thereby forming the adhesive.

The 2-octyl(meth)acrylate is the reaction product of 2-octanol with acrylic acid, and the 2-octanol preferably is biobased, having a $^{14}C/C$ ratio of $1.0 \times 10^{-14}$ or higher.

The adhesive optionally contain further components including in particular a tackifier, a surfactant, a thixotropic agent, and/or a crosslinking agent. Two main types of chemical crosslinking agents are exemplary. The first crosslinking additive is a thermal crosslinking agent such as multifunctional aziridine, isocyanate, oxazole and epoxy compounds. One example of aziridine crosslinker is 1,1'-(1, 3-phenylene dicarbonyl)-bis-(2-methylaziridine) (CAS No. 7652-64-4). Other bisamide crosslinking agents are described in U.S. Pat. No. 6,893,718 (Melancon et al.), incorporated herein by reference. Common polyfunctional isocyanate crosslinkers are trimethylolpropane toluene diisocyanate, toluene diisocyanate, and others known in the art. Such chemical crosslinkers can be added into solvent-based PSAs after polymerization and activated by heat during oven drying of the coated adhesive.

Bisamide crosslinking agents may be of the formula I:

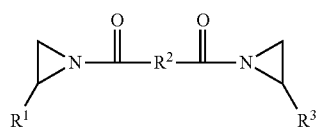

(I)

wherein $R^1$ and $R^3$ are independently selected from the group consisting of H and $C_nH_{2n+1}$, where n is an integer ranging from 1 to 5, $R^2$ is a divalent radical selected from the group consisting of phenyl, substituted phenyl, triazine, and $-C_mH_{2m}-$, where m is an integer ranging from 1 to 10, and combinations thereof.

Useful multifunctional oxazoline crosslinking agents are those that contain two or more groups per molecule selected from the group consisting of 2-oxazolines, 2 oxazines and combinations thereof. Preferred 1,3-oxazyl heterocyclic compounds are 1,3-oxazolines, and a particularly preferred 1,3-oxazoline is 2-phenyl-2-oxazoline. Bisoxazolines are typically derived from polycarboxylic acids and such polycarboxylic acids include, but are not limited to aromatic acids; for example, isophthalic acid, terephthalic acid, 5-t-butylisophthalic acid, trimesic acid, 1,2,4,5-benezenetetracarboxylic acid and 2,6-naphthalene dicarboxylic acid. The preferred polycarboxylic acids include isophthalic acid, terephthalic acid and trimesic acid.

Polyfunctional 1,3-oxazyl heterocyclic compounds useful in this invention can be conveniently prepared by the reaction of the corresponding esters of a polycarboxylic acids and alkanolamines Nonlimiting examples of poly(1, 3-oxazyl heterocyclic) compounds including bisoxazolines are those having a nucleus represented by the following Formula II:

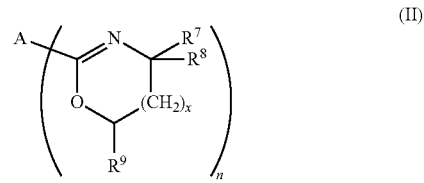

(II)

wherein A is selected from the group consisting of a cyclic or acyclic aliphatic or substituted cyclic or acyclic aliphatic moiety having from 1 to 20 carbon atoms or an aromatic (aryl) mono- or multinuclear or aliphatic substituted aryl residue having from 6 to 20 carbon atoms and a polymeric or oligomeric residue comprising from about 2 to 200,000 repeating units; $R^7$ independently represents H, $CH_3$, $CH_2CH_3$, or $C_6H_5$; $R^8$ and $R^9$ independently represent H or $CH_3$, preferably $R^7$ and $R^9$ are not both $CH_3$; x represents an integer of 0 or 1; and n is an integer of 2 or more, preferably 2 or 3.

Useful multifunctional oxazoline crosslinking agents include but is not limited to 4,4'-5,5'-tetrahydro-2,2'-bisoxazole, (that is, 2,2'-bis(2-oxazoline)); 2,2'-(alkanediyl)bis[4, 5-dihydrooxazole], for example, 2,2'-(1,4-butanediyl)bis[4, 5-dihydrooxazole] and 2,2'-(1,2-ethanediyl)bis[4,5-dihydrooxazole]; 2,2'-(arylene)bis[4,5-dihydrooxazole], e.g., 2,2'-(1,4-phenylene)bis[4,5-dihydrooxazole]; 2,2'-(1,5-naphthalenyl)bis[4,5dihydrooxazole] and 2,2'-(1,8-anthracenyl)bis[4,5-dihydrooxazole]; sulfonyl, oxy, thio or alkylene bis 2-(arylene)[4,5-dihydrooxazole], for example, sulfonyl bis 2-(1,4-phenylene)bis[4,5-dihydrooxazole], oxy-bis 2-(1,4-phenylene)bis[4,5-dihydrooxazole], thiobis 2-(1, 4-phenylene)bis[4,5-dihydrooxazole] and methylene bis 2-(1,4-phenylene)bis[4,5-dihydrooxazole]; 2,2',2"-(arylene tris[4,5-dihydrooxazole], e.g., 2,2',2"-(1,3,5-phenylene tris [4,5-dihydrooxazole]; 2,2',2",2'"-(arylene tetra[4,5-dihydrooxazole], for example, 2,2',2",2'"-(1,2,4,5-phenylene tetra[4,5-dihydrooxazole] and oligomeric and polymeric materials having terminal oxazoline groups.

Typically, the relative amounts of (meth)acrylic acid co-monomer and crosslinking agent are selected so that the ratio of the number of equivalents of crosslinker functional groups (such as amide, oxazole, isocyanate or epoxy functional groups) to the number of equivalents of carboxylic acid groups is less than or equal to about 0.1. More typically, the ratio of the number of equivalents of amide groups to the number of equivalents of carboxylic acid groups is less than about 0.05, and generally will be between 0.0001 and 0.05. Most typically, the ratio of the number of equivalents of crosslinker functional groups to the number of equivalents of carboxylic acid groups will be between 0.0001 and 0.05.

In another embodiment, chemical crosslinkers, which rely upon free radicals to carry out the crosslinking reaction, may be employed. Reagents, for example, peroxides serve as a source of free radicals. When heated sufficiently, these precursors will generate free radicals which bring about a crosslinking reaction of the polymer. A common free radical generating reagent is benzoyl peroxide. Free radical generators are required only in small quantities, but generally require higher temperatures to complete a crosslinking reaction than those required for the bisamide and isocyanate reagents. The second type of crosslinking additive is a photosensitive crosslinker, which is activated by high intensity ultraviolet (UV) light. Two common photosensitive crosslinkers used for (meth)acrylic pressure sensitive adhesives are benzophenone and copolymerizable aromatic ketone monomers as described in U.S. Pat. No. 4,737,559 (Kellen et al.). Another photocrosslinker, which can be post-added to the solution polymer and activated by UV light is a triazine, for example, 2,4-bis(trichloromethyl)-6-(4-methoxy-phenyl)-s-triazine. These crosslinkers are activated by UV light generated from sources such as medium pressure mercury lamps or a UV blacklight.

Useful polyisocyanates include aliphatic, alicyclic, and aromatic diisocyanates, and mixtures thereof. A number of such diisocyanates are commercially available. Representative examples of suitable diisocyanates include hexamethylene diisocyanate (HDT), trimethyl hexamethylene diisocyanate (TMHDI), m- and p-tetramethylxylene diisocyanate (TMXDI), diphenylmethane diisocyanate (MDT), napthalene diisocyanate (NDI), phenylene diisocyanate, isophorone diisocyanate (IPDI), toluene diisocyanate (TDI), bis(4-isocyanatocyclohexyl)methane ($H_{12}$MDI), and the like, and mixtures thereof. Useful polyisocyanates also include derivatives of the above-listed monomeric polyisocyanates. These derivatives include, but are not limited to, polyisocyanates containing biuret groups, such as the biuret adduct of hexamethylene diisocyanate (HDI) available from Bayer Corp., Pittsburgh, Pa. under the trade designation DESMODUR N-100, polyisocyanates containing isocyanurate groups, such as that available from Bayer Corp., Pittsburgh, Pa. under the trade designation DESMODUR N-3300, as well as polyisocyanates containing urethane groups, uretdione groups, carbodiimide groups, allophonate groups, and the like. If desired, small amounts of one or more polyisocyanates having three or more isocyanate groups can be added to effect a degree of crosslinking. Preferred polyisocyanates include aliphatic diisocyanates and derivatives thereof, with IPDI being most preferred.

Hydrolyzable, free-radically copolymerizable crosslinkers, such as monoethylenically unsaturated mono-, di-, and trialkoxy silane compounds including, but not limited to, methacryloxypropyltrimethoxysilane (available from Gelest, Inc., Tullytown, Pa.), vinyl dimethylethoxysilane, vinyl methyl diethoxysilane, vinyltriethoxysilane, vinyltrimethoxysilane, vinyltriphenoxysilane, and the like, are also useful crosslinking agents. Crosslinking may also be achieved using high energy electromagnetic radiation such as gamma or e-beam radiation. In this case, no crosslinker may be required.

Other additives can be included in the adhesive or added at the time of compounding or coating to change the properties of the pressure sensitive adhesive. Such additives include surfactants, pigments, tackifiers, fillers such as glass or polymeric bubbles or beads (which may be expanded or unexpanded), hydrophobic or hydrophilic silica, calcium carbonate, glass or synthetic fibers, blowing agents, toughening agents, reinforcing agents, fire retardants, antioxidants, and stabilizers. The additives are added in amounts sufficient to obtain the desired end properties. In some embodiments, the adhesive includes combinations of thixotropic agents and surfactants, and the like. Examples of thixotropic agents include silica. The adhesive may also contain microspheres such as for example hollow glass bubbles or polymeric microspheres. In some embodiments, the adhesive includes glass bubbles, silica, surfactant, and combinations thereof.

A wide variety of resinous (or synthetic) materials commonly used in the art to impart or enhance tack of pressure sensitive adhesive compositions may be used as a tackifier (i.e., tackifying resin). Examples include rosin, rosin esters of glycerol or pentaerythritol, hydrogenated rosins, polyterpene resins such as polymerized beta-pinene, coumaroneindene resins, "$C_5$" and "$C_9$" polymerized petroleum fractions, and the like. The use of such tack modifiers is common in the art, as is described in the Handbook of Pressure Sensitive Adhesive Technology, Second Edition, D. Satas, ed., Van Nostrand Reinhold, New York, N.Y., 1989. A tackifying resin is added in amounts required to achieve the desired tack level. Examples of suitable commercially available tackifiers include synthetic ester resins, such as that available under the trade designation FORAL 85 from Hercules Inc., Wilmington, Del., and aliphatic/aromatic hydrocarbon resins, such as those available under the trade designation ESCOREZ 2000 from Exxon Chemical Co., Houston, Tex. This is typically achieved by adding from 1 part to about 300 (parts by weight) pbw of tackifying resin per 100 pbw of an acrylate copolymer. The tackifying resin is selected to provide the acrylate copolymers with an adequate degree of tack to maintain the resultant composition balanced pressure sensitive adhesive properties including shear and peel adhesion. As is known in the art, not all tackifier resins interact with the acrylate copolymer in the same manner; therefore, some minor amount of experimentation may be required to select the appropriate tackifier resin and to achieve optimum adhesive performance. Such minor experimentation is well within the capability of one skilled in the adhesive art. If other additives are used, then up to about 40% by weight, preferably less than 30% by weight, and more preferably less than 5% by weight based on the dry weight of the total adhesive polymer, would be suitable.

Examples of monomers that may be co-polymerized with the 2-octyl acrylate include the acrylic acid and/or methacrylic acid, $C_1$-$C_{10}$ (meth)acrylates such as methyl(meth)acrylate, cyclohexyl(meth)acrylate, butyl(meth)acrylates, phenyl(meth)acrylate, primary octyl acrylates such as 2-ethylhexyl acrylate and 6-methylheptyl(meth)acrylate; further examples include N-vinyl pyrrolidone, (meth)acrylamides, alpha-olefins, vinyl ethers, allyl ethers, styrene and other aromatic vinyl compounds, maleic acid esters, 2-hydroxyethyl(meth)acrylate, N-vinyl caprolactam, and substituted (meth)acrylamides such as N-ethyl(meth)acrylamide, N-hydroxyethyl(meth)acrylamide, N-octyl(meth)acrylamide, N-t-butyl(meth)acrylamide, N,N-dimethyl(meth)acrylamide, N,N-diethyl(meth)acrylamide, and N-ethyl-N-dihydroxyethyl(meth)acrylamide.

In an embodiment of the adhesive, the copolymer comprises 60 to less than 90 wt. % of 2-octyl(meth)acrylate, 0.5 to 10 wt. % of (meth)acrylic acid, and 10 to 39.5 wt. % butyl(meth)acrylate. Optionally, the copolymer consists essentially of 60 to less than 90 wt. % of 2-octyl(meth) acrylate, 0.5 to 10 wt. % of (meth)acrylic acid, and 10 to 39.5 wt. % butyl(meth)acrylate.

In the practice of the invention, the copolymers can be polymerized by techniques including, but not limited to, the conventional techniques of solution polymerization, emulsion polymerization, solventless bulk polymerization, and radiation polymerization, including processes using ultraviolet light, electron beam, and gamma radiation. The monomer mixture may comprise a polymerization initiator, especially a thermal initiator or a photoinitiator of a type and in an amount effective to polymerize the comonomers. Initiators useful in preparing the (meth)acrylate adhesive polymers are initiators that, on exposure to heat or light, generate free-radicals which initiate (co)polymerization of the monomer mixture. These initiators can be employed in concentrations ranging from about 0.0001 to about 3.0 pbw, preferably from about 0.001 to about 1.0 pbw, and more preferably from-about 0.005 to about 0.5 pbw, per 100 pbw of the monomer composition.

A typical emulsion polymerization method is carried out by agitating water, monomer, surfactant, initiator, and optionally other additives in the presence of heat (typical temperatures are 50-95° C.). The monomer is understood to migrate into surfactant micelles where it polymerizes into polymer particles.

A typical solution polymerization method is carried out by adding the monomers, a suitable solvent, and an optional chain transfer agent to a reaction vessel, adding a free radical initiator, purging with nitrogen, and maintaining the reaction vessel at an elevated temperature, typically in the range of about 40 to 100° C. until the reaction is completed, typically in about 1 to 20 hours, depending upon the batch size and temperature. Examples of the solvent are methanol, tetrahydrofuran, ethanol, isopropanol, acetone, methyl ethyl ketone, methyl acetate, ethyl acetate, toluene, xylene, and an ethylene glycol alkyl ether. Those solvents can be used alone or as mixtures thereof.

Suitable initiators include but are not limited to those selected from the group consisting of azo compounds such as VAZO 64 (2,2'-azobis(isobutyronitrile)), VAZO 52 (2,2'-azobis(2,4-dimethylpentanenitrile)), and VAZO 67 (2,2'-azobis-(2-methylbutyronitrile)) available from E.I. du Pont de Nemours Co., peroxides such as benzoyl peroxide and lauroyl peroxide, and mixtures thereof. The preferred oil-soluble thermal initiator is (2,2'-azobis-(2-methylbutyronitrile)). When used, initiators may comprise from about 0.05 to about 1 part by weight, preferably about 0.1 to about 0.5 part by weight based on 100 pbw of monomer components in the pressure sensitive adhesive.

In a typical photopolymerization method, a monomer mixture may be irradiated with ultraviolet (UV) rays in the presence of a photopolymerization initiator (i.e., photoinitiators). Preferred photoinitiators are those available under the trade designations IRGACURE and DAROCUR from Ciba Specialty Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis(2,4,6)trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173). Particularly preferred photoinitiators are IRGACURE 819, 184 and 2959.

Solventless polymerization methods, such as the continuous free radical polymerization method described in U.S. Pat. Nos. 4,619,979 and 4,843,134; the essentially adiabatic polymerization methods using a batch reactor described in U.S. Pat. No. 5,637,646; and, the methods described for polymerizing packaged pre-adhesive compositions described in U.S. Pat. No. 5,804,610 may also be utilized to prepare the polymers.

The adhesive may optionally further comprise chain transfer agents to control the molecular weight of the resultant polymer. Examples of useful chain transfer agents include but are not limited to those selected from the group consisting of carbon tetrabromide, alcohols, mercaptans, and mixtures thereof. When present, the preferred chain transfer agents are isooctylthioglycolate and carbon tetrabromide. The adhesive may further comprise up to about 0.5 parts by weight (pbw) of a chain transfer agent, typically about 0.01 to about 0.5 pbw, preferably about 0.05 to about 0.2 pbw, based upon 100 pbw of the total monomer mixture.

Exemplary Embodiments

1. A method of making 2-octyl acrylate comprising reacting 2-octanol with acrylic acid in the presence of an acid catalyst and added water.

2. The method of embodiment 1 wherein the acid catalyst comprises a heterogeneous acid catalyst.

3. The method of embodiment 1 or embodiment 2 wherein functional groups on the acid catalyst comprise sulfonic acid.

4. The method of any one of embodiments 1 through 3 wherein the acid catalyst comprises a cation exchange resin.

5. The method of any one of embodiments 1 through 4 wherein the 2-octanol and acrylic acid are provided in a 10:1 to a 1:10 molar ratio.

6. The method of any one of embodiments 1 through 5 wherein the 2-octanol and acrylic acid are provided in a 3:1 to a 1:3 molar ratio.

7. The method of any one of embodiments 1 through 6 wherein the 2-octanol and acrylic acid are provided in a 1:1 molar ratio.

8. The method of any one of embodiments 1 through 7 wherein the 2-octyl acrylate comprises between 50% and 100% by weight biobased carbon, as determined using ASTM D6866-12.

9. The method of any one of embodiments 1 through 8 wherein the 2-octanol is derived from at least one plant oil.

10. The method of embodiment 9 wherein the 2-octanol is derived from castor oil.

11. The method of any one of embodiments 1 through 10 wherein the added water comprises 0.1 to 10 percent by weight of the total reactants.

12. The method of any one of embodiments 1 through 11 wherein the added water comprises 1 to 5 percent by weight of the total reactants.

13. The method of any one of embodiments 1 through 12 wherein the reaction is performed at a temperature of 60° C. to 130° C.

14. The method of any one of embodiments 1 through 13 wherein the reaction is performed at a temperature of 80° C. to 110° C.

15. The method of any one of embodiments 1 through 14 wherein the reaction is performed in a continuous reactor at a weight hourly space velocity (WHSV) of 0.1 $h^{-1}$ to 3 $h^{-1}$, wherein the WHSV is a ratio of mass flow of 2-octanol and acrylic acid entering the system per hour to the mass of the acid catalyst.

16. The method of any one of embodiments 1 through 15 wherein the reaction is performed in a continuous reactor at a WHSV of 0.3 h$^{-1}$ to 1 h$^{-1}$.

17. The method of any one of embodiments 1 through 16 wherein the reaction is performed at a pressure of atmospheric pressure to 100 pounds per square inch gauge (psig).

18. The method of any one of embodiments 1 through 17 wherein the reaction is performed at a pressure of 10 to 50 psig.

19. The method of any one of embodiments 1 through 18 wherein 15 to 70% by weight of the 2-octanol is converted to 2-octyl acrylate.

20. The method of any one of embodiments 1 through 19 wherein 30 to 70% by weight of the 2-octanol is converted to 2-octyl acrylate.

21. The method of any one of embodiments 1 through 20 further comprising separating unreacted 2-octanol feed from the 2-octyl acrylate using distillation.

22. The method of any one of embodiments 1 through 21 further comprising purifying the 2-octyl acrylate.

23. The method of embodiment 1 wherein the acid catalyst comprises a liquid homogeneous acid catalyst.

24. The method of any one of embodiments 1 through 23 wherein the 2-octanol has a $^{14}$C/C ratio of $1.0 \times 10^{-14}$ or higher.

25. 2-octyl acrylate made by a method comprising reacting 2-octanol with acrylic acid in the presence of an acid catalyst and added water.

26. The 2-octyl acrylate of embodiment 25 wherein the acid catalyst comprises a heterogeneous sulfonic acid catalyst.

27. The 2-octyl acrylate of embodiment 25 wherein the acid catalyst comprises a homogeneous sulfonic acid catalyst.

28. The 2-octyl acrylate of embodiment 26 wherein the acid catalyst comprises a cation exchange resin.

29. The 2-octyl acrylate of any one of embodiments 25 through 28 wherein the 2-octanol and acrylic acid are provided in a 10:1 to 1:10 molar ratio.

30. The 2-octyl acrylate of any one of embodiments 25 through 29 wherein the 2-octanol and acrylic acid are provided in a 1:3 to 3:1 molar ratio.

31. The 2-octyl acrylate of any one of embodiments 25 through 30 wherein the 2-octanol and acrylic acid are provided in a 1:1 molar ratio.

32. The 2-octyl acrylate of any one of embodiments 25 through 31 wherein the 2-octanol is derived from at least one plant oil.

33. The 2-octyl acrylate of any one of embodiments 25 through 32 wherein the 2-octanol is derived from castor oil.

34. A method of making an adhesive comprising:
a. reacting 2-octanol with acrylic acid in the presence of an acid catalyst and added water, thereby forming 2-octyl acrylate; and
b. reacting at least some of the 2-octyl acrylate with at least one initiator and at least one (meth)acrylic acid comonomer, thereby forming the adhesive.

35. The method of embodiment 34, wherein the 2-octyl (meth)acrylate is the reaction product of 2-octyl alcohol with acrylic acid, wherein the 2-octyl alcohol has a $^{14}$C/C ratio of $1.0 \times 10^{-14}$ or higher.

36. The method of embodiment 34 or embodiment 35, wherein the adhesive further comprises a tackifier.

37. The method of any one of embodiments 34 through 36, wherein the adhesive further comprises a plasticizer.

38. The method of any one of embodiments 34 through 37, wherein the adhesive further comprises a crosslinking agent.

39. The method of embodiment 38, wherein the crosslinking agent is selected from the group consisting of peroxides, multifunctional aziridine, isocyanate, oxazole and epoxy compounds.

40. The method of embodiment 34, wherein the (meth) acrylic acid comonomer is selected from the group consisting of acrylic acid, methacrylic acid, and combinations thereof.

41. The method of embodiment 34 wherein said copolymer comprises 60 to less than 90 wt. % of 2-octyl(meth) acrylate, 0.5 to 10 wt. % of (meth)acrylic acid, and 10 to 39.5 wt. % butyl(meth)acrylate.

42. The method of embodiment 34 wherein said copolymer consists essentially of 60 to less than 90 wt. % of 2-octyl(meth)acrylate, 0.5 to 10 wt. % of (meth)acrylic acid, and 10 to 39.5 wt. % butyl(meth)acrylate.

43. An adhesive made according to the method of any one of embodiments 34 through 42.

The operation of the present disclosure will be further described with regard to the following detailed examples. These examples are offered to further illustrate the various specific and preferred embodiments and techniques. It should be understood, however, that many variations and modifications may be made while remaining within the scope of the present disclosure.

EXAMPLES

These Examples are merely for illustrative purposes and are not meant to be overly limiting on the scope of the appended claims. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. At the very least, and not as an attempt to limit the application of the doctrine of equivalents to the scope of the claims, each numerical parameter should at least be construed in light of the number of reported significant digits and by applying ordinary rounding techniques.

Summary of Materials

Unless otherwise noted, all parts, percentages, ratios, etc. in the Examples and the rest of the specification are by weight. Table 1 provides a role and a source for materials used in the Examples below:

TABLE 1

| Role | Material | Source |
| --- | --- | --- |
| Reactant | 2-Octanol | Alfa Aesar, Ward Hill, MA |
| Reactant | Acrylic acid | Alfa Aesar, Ward Hill, MA |
| Catalyst | AMBERLYST 15 | Dow Chemical Company, Midland, MI |
| Catalyst | AMBERLYST 70 | Dow Chemical Company, Midland, MI |
| Catalyst Modifier | Deionized Water | — |

Examples 1-2: 2-Octanol Esterification with AMBERLYST 70 in the Presence of Added Water A 0.5 inch inner diameter (I.D.) by 12 inch length stainless steel reactor tube was charged with 20 grams (g) of AMBERLYST 70 catalyst material (a sulfonated styrene divinylbenzene copolymer). A 1:1 molar ratio of pre-mixed 2-octanol:acrylic acid (the 2-octanol derived from castor oil and the acrylic acid containing 200 ppm hydroquinone monomethyl ether (MEHQ) by weight) containing 5 wt. % added water was fed to the reactor continuously at 1 milliliter per minute (mL min$^{-1}$) total flow rate (0.00420 mole per minute (mol min$^{-1}$) or 0.54712 g min$^{-1}$ of 2-octanol, 0.00420 mol min$^{-1}$ or 0.30274 g min$^{-1}$ of acrylic acid, 0.00248 mol min$^{-1}$ or 0.04473 g min$^{-1}$ of water). The reactor pressure was maintained at approximately 50 pounds per square inch gauge (psig) (0.45 MPa). The reactor temperature was held constant at 90° C. for Example 1 and 120° C. for Example 2. After allowing at least three residence times (e.g., a total of about 45 minutes) to reach steady state, product was collected for analysis and found to contain primarily a mixture of octanol isomers, acrylic acid, octene isomers, and octyl acrylate isomers.

Conversion of 2-octanol, octyl acrylate yield, and octene yield for Example 1 were 6.4%, 6.3% and 0.1%, respectively. Conversion of 2-octanol, octyl acrylate yield, and octene yield for Example 2 were 23.7%, 20.9% and 2.8%, respectively. Octyl acrylate yield is defined to be the ratio of molar flow rate of octyl acrylate out of the reactor divided by molar flow rate of 2-octanol into the reactor. Octene yield is defined to be the ratio of molar flow rate of octene out of the reactor divided by molar flow rate of 2-octanol into the reactor. Selectivities to octyl acrylate product for Example 1 and Example 2 were 98.4% and 88.1%, respectively. All of the results are provided below in Table 2.

Example 3: High Yield and Selectivity for 2-Octyl Acrylate

A 0.5 inch I.D. by 12 inch length stainless steel reactor tube was charged with 20 g of AMBERLYST 70 catalyst material (a sulfonated styrene divinylbenzene copolymer). A 1:1 molar ratio of pre-mixed 2-octanol:acrylic acid (the 2-octanol derived from castor oil and the acrylic acid containing 200 ppm MEHQ by weight) containing 1 wt. % added water was fed to the reactor continuously at 0.2 mL min$^{-1}$ total flow rate (0.00436 mol min$^{-1}$ or 0.56764 g min$^{-1}$ of 2-octanol, 0.00436 mol min$^{-1}$ or 0.31409 g min$^{-1}$ of acrylic acid, 0.00049 mol min$^{-1}$ or 0.00891 g min$^{-1}$ of water) and reactor pressure was maintained at approximately 50 psig (0.45 MPa). The reactor temperature was held constant at 90° C. After allowing at least three residence times (e.g., a total of about 3 hours) to reach steady state, product was collected for analysis and found to contain primarily a mixture of octanol, acrylic acid, octene isomers, water, and octyl acrylate isomers. Conversion of 2-octanol, octyl acrylate yield, and octene yield for were 33.1%, 30.7%, and 2.4%, respectively. Selectivity to octyl acrylate product was 92.7%. All of the results are provided below in Table 2.

Comparative Examples 4-6: 2-Octanol Esterification with AMBERLYST 15 in the Absence of Added Water A 0.75 inch I.D. by 18 inch length stainless steel reactor tube was charged with 42.6 g of AMBERLYST 15 Dry catalyst material (a sulfonated styrene divinylbenzene copolymer). A 1:1 molar ratio of pre-mixed 2-octanol:acrylic acid (the 2-octanol derived from castor oil and acrylic acid containing 200 ppm MEHQ by weight) was fed to the reactor continuously at 1 mL min$^{-1}$ total flow rate (0.00439 mol min$^{-1}$ or 0.57274 g min$^{-1}$ of 2-octanol, 0.00439 mol min$^{-1}$ or 0.31691 g min$^{-1}$ of acrylic acid) and reactor pressure was maintained at approximately 100 psig (0.79 MPa). Reactor temperature was held constant at 80° C. for Comparative Example 4, 100° C. for Comparative Example 5 and 120° C. for Comparative Example 6. After allowing at least three residence times (e.g., a total of about 1.5 hours) to reach steady state, product was collected for analysis and found to contain primarily a mixture of octanol isomers, acrylic acid, octene isomers, water, and octyl acrylate isomers.

Conversion of 2-octanol, octyl acrylate yield, and octene yield for Comparative Example 4 were 10.9%, 5.5% and 5.4%, respectively. Conversion of 2-octanol, octyl acrylate yield, and octene yield for Comparative Example 5 were 40.4%, 16.7% and 23.7%, respectively. Conversion of 2-octanol, octyl acrylate yield, and octene yield for Comparative Example 6 were 64.7%, 27.3% and 37.3%, respectively. Selectivities to octyl acrylate product for Comparative Example 4, Comparative Example 5 and Comparative Example 6 were 50.5%, 41.3% and 42.2%, respectively. All of the results are provided below in Table 2.

Comparative Examples 7-8: 2-Octanol Esterification with AMBERLYST 70 in the Absence of Added Water A 0.5 in I.D. by 12 in length stainless steel reactor tube was charged with 20 g of AMBERLYST 70 catalyst material (a sulfonated styrene divinylbenzene copolymer). A 1:1 molar ratio of pre-mixed 2-octanol:acrylic acid (the 2-octanol derived from castor oil and acrylic acid containing 200 ppm MEHQ by weight) was fed to the reactor continuously at 1 mL min$^{-1}$ total flow rate (0.00439 mol min-1 or 0.57274 g min-1 of 2-octanol, 0.00439 mol min-1 or 0.31691 g min-1 of acrylic acid) and reactor pressure was maintained at approximately 50 psig (0.45 MPa). Reactor temperature was held constant at 90° C. for Comparative Example 7 and 120° C. for Comparative Example 8. After allowing at least three residence times (e.g., a total of about 45 minutes) to reach steady state, product was collected for analysis and found to contain primarily a mixture of octanol isomers, acrylic acid, octene isomers, water, and octyl acrylate isomers.

Conversion of 2-octanol, octyl acrylate yield, and octene yield for Comparative Example 7 were 13.5%, 11.6% and 1.9%, respectively. Conversion of 2-octanol, octyl acrylate yield, and octene yield for Comparative Example 8 were 45.7%, 32.7% and 13%, respectively. Selectivities to octyl acrylate product for Comparative Example 7 and Comparative Example 8 were 86.2% and 71.5%, respectively.

TABLE 2

|  | Ex. 1 | Ex. 2 | Ex. 3 | C. Ex. 4 | C. Ex. 5 | C. Ex. 6 | C. Ex. 7 | C. Ex. 8 |
| --- | --- | --- | --- | --- | --- | --- | --- | --- |
| Water | 5% | 5% | 1% | 0% | 0% | 0% | 0% | 0% |
| Temperature | 90° C. | 120° C. | 90° C. | 80° C. | 100° C. | 120° C. | 90° C. | 120° C. |
| Pressure (psig) | 50 | 50 | 50 | 100 | 100 | 100 | 50 | 50 |

TABLE 2-continued

|  | Ex. 1 | Ex. 2 | Ex. 3 | C. Ex. 4 | C. Ex. 5 | C. Ex. 6 | C. Ex. 7 | C. Ex. 8 |
|---|---|---|---|---|---|---|---|---|
| Conversion | 20.9% | 2.8% | 33.1% | 10.9% | 40.4% | 64.7% | 13.5% | 45.7% |
| OA Yield | 6.3% | 20.9% | 30.7% | 5.5% | 16.7% | 27.3% | 11.6% | 32.7% |
| Octene Yield | 0.1% | 2.8% | 2.4% | 5.4% | 23.7% | 37.3% | 1.9% | 13% |
| Selectivity | 98.4% | 88.1% | 92.7% | 50.5% | 41.3% | 42.2% | 86.2% | 71.5% |

Examples 9-11: Adhesive Preparation (Prophetic)

A method for making an adhesive comprises reacting 2-octanol with acrylic acid in the presence of an acid catalyst and added water to form 2-octyl acrylate; and reacting at least some of the 2-octyl acrylate with at least one initiator and at least one (meth)acrylic acid comonomer to form the adhesive. For Example 9, Example 10, and Example 11, solution co-polymerizations of 2-octyl acrylate with acrylic acid and ethyl acetate are performed by combining the 2-octyl acrylate made in Example 7 with the materials shown in Table 3 in a glass jar, purging with nitrogen for 15 minutes, and sealing the jars. The jars are placed in a 60° C. water bath oscillating at 110 rpm for 18-24 hours to polymerize the adhesive. Each of the acrylic acid, initiator VAZO 67, and ethyl acetate are commercially available from Sigma-Aldrich Chemical Company; Milwaukee, Wis.

TABLE 3

|  | Ex. 9 | Ex. 10 | Ex. 11 |
|---|---|---|---|
| 2-OA (grams) | 17.10 | 19.95 | 22.8 |
| Acrylic Acid (grams) | 0.90 | 1.05 | 1.20 |
| VAZO 67 (2,2'-azobis-(2-methylbutyronitrile)) (grams) | 0.018 | 0.021 | 0.024 |
| Ethyl Acetate (grams) | 42.0 | 39.0 | 36.0 |

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A method of making 2-octyl acrylate comprising reacting 2-octanol with acrylic acid in the presence of an acid catalyst and added water.

2. The method of claim 1 wherein the acid catalyst comprises a heterogeneous acid catalyst.

3. The method of claim 1 wherein functional groups on the acid catalyst comprise sulfonic acid.

4. The method of claim 3 wherein the acid catalyst comprises a cation exchange resin.

5. The method of claim 1 wherein the 2-octanol and acrylic acid are provided in a 3:1 to a 1:3 molar ratio.

6. The method of claim 1 wherein the 2-octyl acrylate comprises between 50% and 100% by weight biobased carbon, as determined using ASTM D6866-12.

7. The method of claim 6 wherein the 2-octanol is derived from castor oil.

8. The method of claim 1 wherein the added water comprises 1 to 5 percent by weight of the total reactants.

9. The method of claim 1 wherein the reaction is performed at a temperature of 60° C. to 130° C.

10. The method of claim 1 wherein the reaction is performed in a continuous reactor at a weight hourly space velocity (WHSV) of 0.1 h$^{-1}$ to 3 h$^{-1}$, wherein the WHSV is a ratio of mass flow of 2-octanol and acrylic acid entering the system per hour to the mass of the acid catalyst.

11. The method of claim 1 wherein 15 to 70% by weight of the 2-octanol is converted to 2-octyl acrylate.

12. The method of claim 1 wherein the acid catalyst comprises a liquid homogeneous acid catalyst.

13. The method of claim 1 wherein the 2-octanol has a $^{14}$C/C ratio of $1.0 \times 10^{-14}$ or higher.

14. A method of making an adhesive comprising:
 a. reacting 2-octanol with acrylic acid in the presence of an acid catalyst and added water, thereby forming 2-octyl acrylate; and
 b. reacting at least some of the 2-octyl acrylate with at least one initiator and at least one (meth)acrylic acid comonomer, thereby forming the adhesive.

15. The method of claim 14, wherein the 2-octyl acrylate is the reaction product of 2-octanol with acrylic acid, wherein the 2-octanol has a $^{14}$C/C ratio of $1.0 \times 10^{-14}$ or higher.

* * * * *